(12) United States Patent
McNeff

(10) Patent No.: US 7,943,791 B2
(45) Date of Patent: May 17, 2011

(54) METHODS AND COMPOSITIONS FOR REFINING LIPID FEED STOCKS

(75) Inventor: Clayton V. McNeff, Andover, MN (US)

(73) Assignee: McNeff Research Consultants, Inc., Anoka, MN (US)

(*) Notice: Subject to any disclaimer, the term of this patent is extended or adjusted under 35 U.S.C. 154(b) by 0 days.

(21) Appl. No.: 12/238,750

(22) Filed: Sep. 26, 2008

(65) Prior Publication Data
US 2009/0112008 A1    Apr. 30, 2009

Related U.S. Application Data

(60) Provisional application No. 60/976,174, filed on Sep. 28, 2007.

(51) Int. Cl.
*C07C 51/43*  (2006.01)
(52) U.S. Cl. ........................... 554/174; 554/124
(58) Field of Classification Search ............ 554/124, 554/174
See application file for complete search history.

(56) References Cited

U.S. PATENT DOCUMENTS

| | | | |
|---|---|---|---|
| 2,383,632 A | 8/1945 | Trent | |
| 2,679,471 A | 5/1954 | Ayers et al. | |
| 3,383,396 A | 5/1968 | Cahn et al. | |
| 4,138,336 A | 2/1979 | Mendel et al. | |
| 4,216,337 A | 8/1980 | Baba et al. | |
| 4,487,933 A | 12/1984 | Mixan et al. | |
| 4,582,589 A | 4/1986 | Ushizawa et al. | |
| 4,716,218 A | 12/1987 | Chen et al. | |
| 4,861,739 A | 8/1989 | Pellet et al. | |
| 5,108,597 A | 4/1992 | Funkenbusch et al. | |
| 5,182,016 A | 1/1993 | Funkenbusch et al. | |
| 5,254,262 A | 10/1993 | Funkenbusch et al. | |
| 5,271,833 A | 12/1993 | Funkenbusch et al. | |
| 5,298,650 A | 3/1994 | Walter et al. | |

(Continued)

FOREIGN PATENT DOCUMENTS

BR    8202429    11/1983

(Continued)

OTHER PUBLICATIONS

File History in co-pending U.S. Appl. No. 11/833,839, Entitled "Methods and Apparatus for Producing Alkyl Esters from Lipid Feed Stocks and Systems Including Same" (pp. 1-234).

(Continued)

*Primary Examiner* — Deborah D Carr
(74) *Attorney, Agent, or Firm* — Pauly, DeVries Smith & Deffner, L.L.C.

(57) ABSTRACT

The present invention relates to systems and methods of using fatty acid alkyl ester solutions to refine feed stocks before converting the feed stocks into fatty acid fatty acid alkyl esters. In an embodiment, the invention includes a method for producing fatty acid alkyl esters. The method can include mixing a crude lipid feed stock with a refining solution to form a crude product mixture, the refining solution comprising greater than about 10 wt. % fatty acid alkyl esters. The method can include extracting the liquid phase from the crude product mixture to obtain a purified lipid feed stock. The method can also include reacting the purified lipid feed stock with an alcohol to form a product mixture comprising fatty acid alkyl esters. In an embodiment, the invention includes a method of making a fatty acid alkyl ester composition. The method can include extracting lipids from a corn-based ethanol production byproduct, adding an alcohol solution to the lipids to form a reaction mixture, and contacting the reaction mixture with a metal oxide catalyst. Other embodiments are included herein.

18 Claims, 2 Drawing Sheets

U.S. PATENT DOCUMENTS

| | | | |
|---|---|---|---|
| 5,321,197 A | 6/1994 | Angstadt et al. | |
| 5,346,619 A | 9/1994 | Funkenbusch et al. | |
| 5,350,879 A | 9/1994 | Engel et al. | |
| 5,508,457 A | 4/1996 | Bayense et al. | |
| 5,532,392 A | 7/1996 | Gheorghiu | |
| 5,540,834 A | 7/1996 | Carr et al. | |
| 5,908,946 A | 6/1999 | Stern et al. | |
| 6,090,959 A | 7/2000 | Hirano et al. | |
| 6,211,390 B1 | 4/2001 | Peter et al. | |
| 6,376,701 B1 | 4/2002 | Chavan et al. | |
| 6,392,062 B1 | 5/2002 | Haas | |
| 6,433,146 B1 | 8/2002 | Cheryan | |
| 6,489,496 B2 | 12/2002 | Barnhorst et al. | |
| 6,538,146 B2 | 3/2003 | Turck | |
| 6,666,074 B2 | 12/2003 | Gerner et al. | |
| 6,712,867 B1 | 3/2004 | Boocock | |
| 6,719,815 B2 | 4/2004 | Nanninga et al. | |
| 6,768,015 B1 | 7/2004 | Luxem et al. | |
| 6,878,837 B2 | 4/2005 | Bournay et al. | |
| 6,887,283 B1 | 5/2005 | Ginosar et al. | |
| 6,960,672 B2 | 11/2005 | Nakayama et al. | |
| 6,963,004 B2 | 11/2005 | Ahtchi-Ali et al. | |
| 6,965,044 B1 | 11/2005 | Hammond et al. | |
| 6,979,426 B2 | 12/2005 | Teall et al. | |
| 6,982,340 B2 | 1/2006 | Mumura et al. | |
| 7,045,100 B2 | 5/2006 | Ergun et al. | |
| 7,112,688 B1 | 9/2006 | Tysinger et al. | |
| 7,145,026 B2 | 12/2006 | Fleisher | |
| 7,151,187 B2 | 12/2006 | Delfort et al. | |
| 7,211,681 B2 | 5/2007 | Furuta | |
| 7,321,052 B2 | 1/2008 | Miller et al. | |
| 7,498,454 B2 | 3/2009 | Relingshoefer | |
| 7,563,915 B2 | 7/2009 | Matson | |
| 7,582,784 B2 | 9/2009 | Vali | |
| 7,601,858 B2 | 10/2009 | Cantrell et al. | |
| 7,790,651 B2 | 9/2010 | Lin | |
| 2002/0010359 A1 | 1/2002 | Kaita et al. | |
| 2002/0156305 A1 | 10/2002 | Turck | |
| 2003/0229238 A1 | 12/2003 | Fleisher | |
| 2004/0074760 A1 | 4/2004 | Portnoff et al. | |
| 2004/0087809 A1 | 5/2004 | Nakayama et al. | |
| 2005/0064577 A1 | 3/2005 | Berzin | |
| 2005/0080280 A1 | 4/2005 | Yoo | |
| 2005/0118409 A1 | 6/2005 | McNeff et al. | |
| 2005/0137411 A1 | 6/2005 | Ahtchi-Ali et al. | |
| 2005/0204612 A1 | 9/2005 | Connemann et al. | |
| 2005/0239182 A1 | 10/2005 | Berzin | |
| 2005/0260553 A1 | 11/2005 | Berzin | |
| 2005/0261509 A1 | 11/2005 | Delfort et al. | |
| 2005/0266139 A1 | 12/2005 | Lacome et al. | |
| 2005/0274065 A1 | 12/2005 | Portnoff et al. | |
| 2006/0014974 A1 | 1/2006 | Bournay et al. | |
| 2006/0041152 A1 | 2/2006 | Cantrell et al. | |
| 2006/0041153 A1 | 2/2006 | Cantrell et al. | |
| 2006/0080891 A1 | 4/2006 | Ghosh et al. | |
| 2006/0149087 A1 | 7/2006 | Furuta | |
| 2006/0224005 A1 | 10/2006 | Felly | |
| 2006/0252950 A1 | 11/2006 | Ginosar et al. | |
| 2006/0260186 A1 | 11/2006 | Iversen et al. | |
| 2006/0288636 A1 | 12/2006 | Iijima et al. | |
| 2007/0010682 A1 | 1/2007 | Myllyoja et al. | |
| 2007/0037994 A1 | 1/2007 | Canos et al. | |
| 2007/0027338 A1 | 2/2007 | Furuta | |
| 2007/0066838 A1 | 3/2007 | Hillion et al. | |
| 2007/0089356 A1 | 4/2007 | Krasutsky et al. | |
| 2007/0093380 A1 | 4/2007 | Srinivas et al. | |
| 2007/0196892 A1 | 8/2007 | Winsness et al. | |
| 2007/0283619 A1 | 12/2007 | Hillion et al. | |
| 2008/0051592 A1 | 2/2008 | McNeff et al. | |
| 2008/0161615 A1 | 7/2008 | Chapus | |
| 2008/0188676 A1 | 8/2008 | Anderson et al. | |
| 2008/0197052 A1 | 8/2008 | McNeff et al. | |
| 2008/0318763 A1 | 12/2008 | Anderson | |
| 2009/0029445 A1 | 1/2009 | Eckelberry et al. | |
| 2010/0087670 A1 | 4/2010 | Wang et al. | |

FOREIGN PATENT DOCUMENTS

| | | |
|---|---|---|
| CN | 1680514 | 10/2005 |
| CN | 1718679 | 1/2006 |
| CN | 1858160 | 11/2006 |
| CN | 1887417 | 1/2007 |
| CN | 1928016 | 3/2007 |
| DE | 102005038137 | 2/2007 |
| EP | 0198243 | 10/1986 |
| EP | 0507217 | 10/1992 |
| EP | 0535290 | 4/1993 |
| EP | 1505048 | 2/2005 |
| EP | 1580255 | 9/2005 |
| EP | 1607467 | 12/2005 |
| EP | 1681281 | 7/2006 |
| FR | 2188612 | 1/1974 |
| FR | 2679471 | 1/1993 |
| FR | 2890656 | 3/2007 |
| GB | 2132222 | 7/1984 |
| JP | 6313188 | 11/1994 |
| JP | 11228494 | 8/1999 |
| JP | 2005126346 | 5/2005 |
| JP | 2005177722 | 7/2005 |
| JP | 2007153943 | 6/2007 |
| JP | 2007190450 | 8/2007 |
| JP | 2008111085 | 5/2008 |
| WO | WO-0005327 | 2/2000 |
| WO | WO-03/062358 | 7/2003 |
| WO | WO-03/087279 | 10/2003 |
| WO | WO-03094598 | 11/2003 |
| WO | WO-2004/085585 | 10/2004 |
| WO | WO-2004096962 | 11/2004 |
| WO | WO-2005/021697 | 3/2005 |
| WO | WO-2005021697 | 3/2005 |
| WO | WO-2005/123890 | 12/2005 |
| WO | WO-2006/070661 | 7/2006 |
| WO | WO-2006/081644 | 8/2006 |
| WO | WO-2006/088254 | 8/2006 |
| WO | WO-2006/093896 | 9/2006 |
| WO | WO-2006/094986 | 9/2006 |
| WO | WO-2007/011343 | 1/2007 |
| WO | WO-2007/012190 | 2/2007 |
| WO | WO-2007/025360 | 3/2007 |
| WO | WO-2007/029851 | 3/2007 |
| WO | WO-2007/038605 | 4/2007 |
| WO | WO-2007/043062 | 4/2007 |
| WO | WO-2007072972 | 6/2007 |
| WO | WO-2007077950 | 7/2007 |
| WO | WO-2007/111604 | 10/2007 |
| WO | WO-2007/140395 | 12/2007 |
| WO | WO-2007/141293 | 12/2007 |
| WO | WO-2007/142983 | 12/2007 |
| WO | WO-2008012275 | 1/2008 |
| WO | WO-2008019325 | 2/2008 |
| WO | WO-2008/034109 | 3/2008 |
| WO | WO-2008029132 | 3/2008 |
| WO | WO-2008041038 | 4/2008 |
| WO | WO-2008101032 | 8/2008 |

OTHER PUBLICATIONS

File History in co-pending U.S. Appl. No. 12/030,801, Entitled "Devices and Methods for Selective Removal of Contaminants from a Composition" (pp. 1-237).

International Search Report and Written Opinion from International Application No. PCT/US2008/053883, mailed Jul. 9, 2008 (pp. 1-13).

PCT International Search Report and Written Opinion from International Application No. PCT/US2007/075211, mailed Jul. 9, 2008 (pp. 1-14).

U.S. Appl. No. 61/088,602, Entitled "Systems for Selective Removal of Contaminants From a Composition and Methods of Regenerating the Same", Filed on Aug. 13, 2008.

U.S. Appl. No. 61/103,513, Entitled "Catalysts, Systems, and Methods for Producing Fuels and Fuel Additives From Polyols", Filed on Oct. 7, 2008.

U.S. Appl. No. 61/113,854, Entitled "Systems and Methods for Producing Fuels from Biomass", Filed on Nov. 12, 2008.

U.S. Appl. No. 61/139,684, Entitled "Systems and Methods for Producing Fuels and Fuel Precursors from Carbohydrates", Filed on Dec. 22, 2008.
"EP Communication, EPO form 2906 01.91TRI, from the European Patent Office in EP Patent Application No. 07840692.3, corresponding to U.S. Appl. No. 11/833,839, mailed Dec. 11, 2009, (pp. 1-4)".
"EP Communication, EPO form 2906 01.91TRI, from the European Patent Office in EP Patent Application No. 08729792.5, corresponding to U.S. Appl. No. 12/030,801, mailed Mar. 2, 2010, (pp. 1-4)".
"Kyte Centrifuge Sales & Consulting", www.kcentrifuge.com, p. 1.
Annen, et al., "Development of Porous Zirconia Spheres by Polymerization-Induced Colloid Aggregation-Effect of Polymerization Rate", Journal of Mater. Sci.,29(23):6123-6130 (1994).
Annon, , "Beatrice Biodiesel Selects Axens Exterfip-H Technology", Biodiesel Magazine Jun. 2006, Unknown.
BCC Research, , "Global Market for Catalyst Regeneration", MarketResearch.com http://www.marketresearch.com/product/display.asp?productid=1354464 2006 , 1-20.
Blackwell, J. A. et al., "A Chromatographic Study of the Lewis Acid-Base Chemistry of Zirconia Surfaces", J. Liquid Chromatog. 1991 , 14: 2875-2889.
Blackwell, J. A. et al., "Study of the Fluoride Adsorption Characterisitics of Porous Microparticulate Zirconium Oxide", J. Chromatog. 1991 , 549: 43-57.
Bournay, L. et al., "New Heterogeneous Process for Biodiesel Production: A Way to Improve the Quality and the Value of the Crude Glycerin Produced by Biodiesel Plants", Catalysis Today 2005 , 106: 190-192.
Brown, Adrian S. et al., "Sulfated Metal Oxide Catalysts: Superactivity through Superacidity?", Green Chemistry Feb. 1999 , 17-20.
Bryan, Tom , "Adsorbing It All", Biodiesel Magazine Mar. 2005 , 40-43.
Cao, W. et al., "Preparation of Biodiesel from Soybean Oil Using Supercritical Methanol and Co-Solvent", Fuel 2005 , 84: 347-351.
Collins, K. , "Statement of Keith Collins, Chief Economist, U.S. Department of Agriculture before the U.S. Senate Committee on Appropriations, Subcommittee on Agriculture, Rural Development, and Related Agencies: Economic Issues Related to Biofuels.", Unknown www.usda.gov/documents/Farmbill07energy.doc. Aug. 26, 2006, 1-8 (web).
Dean, Morgan et al., "Nanocrystalline Metal Oxide-Based Catalysts for Biodiesel Production from Soybean Oil", #96—Student Poster Session: Catalysis & Reaction Engineering (04016) http://aiche.confex.com/aiche/2006/techprogram/P78366.HTM Nov. 13, 2006, 1 (web).
Demirbas, Ayhan , "Biodiesel fuels from vegetable oils via catalytic and non-catalytic supercritical alcohol transesterifications and other methods: a survey", Energy Conversion & Management 2003 , issue 44 pp. 2093-2109.
Di Serio, et al., "Synthesis of Biodiesel via Homogeneous Lewis Acid Catalyst", J. Molec. Catal. A Chem. 2005 , 239: 111-115.
Di Serio, M. et al., "Transesterification of Soybean Oil to Biodiesel by Using Heterogeneous Basic Catalysts", Ind. Eng. Chem. Res. 2006 , 45: 3009-3014.
Dorsa, Renato et al., "Basics of Alkali Refining of Vegetable Oils", GEA Westfalia Separator Food Tec GmbH Unknown , 1-28.
Dunlap, C. J. et al., "Zirconia Stationary Phases for Extreme Separations", Anal. Chem. 2001 , 73: 598A.-607A.
Elliott, Brian , "Low-cost Biodiesel Production Process Using Waste Oils and Fats", U.S. EPA SBIR Phase I Kick-Off Meeting www.iastate.edu/Inside/2003/0613/biorenewable.jpg Apr. 5, 2007, 1.
Furuta, S. et al., "Biodiesel Fuel Production with Solid Superacid Catalysis is Fixed Bed Reactor Under Atmospheric Pressure", Catalysis Communications 2004, 5: 721-723.
Gercel, H. F. et al., "Hydropyrolysis of Extracted Euphorbia rigida in a Well-Swept Fixed-Bed Tubular Reactor", Energy Sources 2002 , 24: 423-430.
Goering, C. E. et al., "Fuel Properties of Eleven Vegetable Oils", Trans ASAE 1982, 25: 1472-1477.
Goodwin, J. G. , "Research Activities: Biodiesel Synthesis", Chemical and Biomolecular Engineering at Clemson University http://www.ces.clemson.edu/chemeng/facultypages/goodwin/research.html 2006 , 1-5.

Haas, M. J. et al., "Engine Performance of Biodiesel Fuel Prepared from Soybean Soapstack: A High Quality Renewable Fuel Produced from a Waste Feedstock", Energy Fuels 2001 , 15: 1207-1212.
Haas, M. J. et al., "Improving the Economics of Biodiesel Production Through the Use of Low Value Lipids as Feedstocks: Vegetable Oil soapstock", Fuel Process. Technol. 2005, 86: 1087-1096.
Harvey, A. P. et al., "Process Intensification of Biodiesel Production Using a Continuous Oscillatory Flow Reactor", J. Chem. Technol. Biotechnol. 2003 , 78: 338-341.
He, Chen et al., "Biodiesel from Transesterification of Cotton Seed Oil by Solid Bases Catalysis", Journal of Chemical Engineering of Chinese Universities Aug. 2006, No. 4 vol. 20.
He, Chen et al., "Biodiesel Production by the transesterification of cottonseed oil by solid acid catalysts", Frontiers of Chemical Engineering in China Feb. 2007 , vol. 1, No. 1, pp. 1673-7369.
Henry, R. A. et al., "A Novel Chemical Route to Stable, Regenerable Zirconia-Based Chiral Stationary Phases for HPLC", American Laboratory (News Edition) 2005 , 37: 22-24.
Hill, J. et al., "Environmental, Economic, and Energetic Costs and Benefits of Biodiesel and Ethanol Biofuels", PNAS 2006 , 103(30): 11206-11210.
Iijima, Wataru et al., ""Winterized" Bio-Diesel Fuel Produced from Animal Fat", Agro-Energy Laboratory, Dept. Of Farm Mechanization and Engineering, National Agricultural ResearchCentre, National Agricultural Research Organization, Japan Unknown, 1-2.
Iijima, Wataru et al., "The Non-glycerol Process of Biodiesel Fuel Treated in Supercritical Methanol (Abstract)", Paper No. 046073, 2004 ASAE Annual Meeting 2004, 1.
Ishihara, K. et al., "Direct Ester Condensation from a 1:1 Mixture of Carboxylic Acids and Alcohols Catalyzed by Hafnium (IV) or Zirconium (IV) Salts.", Tetrahedron 2002 , 58: 8179-8188.
Kahn, A. , "Research into Biodiesel Catalyst Screening and Development", Thesis, University of Queensland Brisbane 2002 , 1-41.
Kiss, Anton A. et al., "Solid Acid Catalysts for Biodiesel Production—Towards Sustainable Energy", Adv. Synth. Catal. 2006 , 348: 75-81.
Knothe, G. , "Analytical Methods Used in the Production and Fuel Quality Assessment of Biodiesel", Transactions of the ASAE 2001 , 44(2): 193-200.
Knothe, Gerhard et al., "Bidiesel: The Use of Vegetable Oils and Their Derivatives as Alternative Diesel Fuels", Oil Chemical Research, National Center for Agricultural Utilization Research, Agricultural Research Service, U.S. Department of Agriculture Peoria, IL 61604 Unknown , 1-36.
Koh, Ashley D. , "Non-Catalytic Biodiesel Production from Soybean Oil Using Supercritical Methanol", The 2006 Annual Meeting San Francisco, CA http://aiche.confex.com/aiche/2006/techprogram/P69978.HTM presented Nov. 15, 2006, 1.
Kulkarni, Mangesh G. et al., "Solid Acid Catalyxed Biodiesel Production by Simultaneous Esterification and Transesterification", Green Chem. 2006 , 8: 1056-1062.
Kulkarni, M. et al., "Waste Cooking Oil: An Economical Source for Biodiesel", Ind. Eng. Chem. Res. 2006 , 45: 2901-2913.
Liu, Yijun et al., "Transesterification of Poultry Fat with Methanol Using Mg-Al Hydrotalcite Derived Catalysts", Applied Catalysis A: General (Abstract only) 2007, vol. 331, 138-148.
Lopez, Dora E. et al., "Esterification and transesterification on tungstated zirconia: Effect of calcination temperature", Journal or Catalysis Apr. 1, 2007 , vol. 247, Iss. 1, 43-50.
Lopez, D.E. et al., "Transesterification of Triacetin with Methanol on Solid Acid and Base Catalysts", Appl. Catalysis A: General 2005 , 295: 97-105.
Lotero, E. et al., "Synthesis of Biodiesel Via Acid Catalysis", Ind. Eng. Chem. Res. 2005 , 44:5353-5363.
Ma, R et al., "Biodiesel Production: A Review", Bioresource Technol. 1999 , 70:1-15.
Miller, Dennis J. et al., "Catalysis for Biorenewables Conversion", National Science Foundation Workshop Report www.egr.msu.edu/apps/nsfworkshop Apr. 13, 2004 , 1-63 (web).
Mittelbach, Martin et al., "Diesel Fuel Derived from Vegetable Oils, III. Emission Tests Using Methyl Esters of Used Frying Oil", JAOCS Jul. 1988, vol. 65, No. 7, 1185-1187.

Nawrocki, J. et al., "Chemistry of Zirconia and Its Use in Chromatography", *J. Chromatog.* 1993, A 657: 229-282.

Omota, F. et al., "Fatty Acid Esterification by Reactive Distillation: Part 2—Kinetics-based Design for Sulphated Zirconia Catalysts", *Chemical Engineering Science* 2003, 58: 3175-3185.

Ondrey, G., "Biodiesel Production Using a Heterogeneous Catalyst", *Chemical Engineering* 2004, 111(11):13.

Otera, J., "Transesterification", *Chem. Rev.* 1993, 93:1449-1470.

Peterson, C. L. et al., "Continuous Flow Biodiesel Production", *Appl. Eng. Agricul.* 2002, 18: 5-11.

Pinto, A. C. et al., "Biodiesel: An Overview", *J. Braz. Chem. Soc.* 2005, 16: 1313-1330.

Pruszko, R., "Strategic Biodiesel Decisions", *Iowa State University—University Extension* CIRAS 2006, 1-32.

Raddi De Araujo, Lucia R. et al., "H3PO4/Al2O3 Catatysts: Characterization and Catalytic Evaluation of Oleic Acid Conversion to Biofuels and Biolubricant", *Materials Research* 2006, vol. 9, No. 2, 181-184.

Reisch, Marc S., "Start-up Firms Pursue Biofuels", *Chemical & Engineering News* Nov. 20, 2006, vol. 84, No. 47, 1-2(web).

Rigney, M. P. et al., "Physical and Chemical Characterization of Microporous Zirconia", *J. Chromatog* 1990, 499: 291-304.

Schuchardt, Ulf et al., "Transesterification of Vegetable Oils: a Review", *J. Braz. Chem. Soc.* 1998, vol. 9, No. 1, 199-210.

Silva, Lisa et al., "Colorado Diesel School Bus Retrofit Program", *A Cooperative Effort of the Regional Air Quality Council and the Colorado Department of Public Health and Environment* 2006, 1-17.

Suppes, G. J. et al., "Transesterification of Soybean Oil with Zeolite and Metal Catalysts", *Applied Catalysis A: General* 2004, 257: 213-223.

Suwannakarn, Kaewta et al., "A comparative study of gas phase esterification on solid acid catalysts", *Catalysis Letters* Apr. 2007, vol. 114, Nos. 3-4, 1-7.

Tyson, K. S., "Brown Grease Feedstocks for Biodiesel", *National Renewable Energy Laboratory* Jun. 19, 2002, 1-34.

Unknown, "AMBERLITEtm FP Ion Exchange Resins", *Amberlite FP technical bulletin* http://www.advancedbiosciences.com Dec. 2004, 1-7.

Unknown, et al., "Oak Ridge lab develops materials for biodiesel catalysis", *Biodiesel Magazine* http://biodieselmagazine.com/article-print.jsp?article$_{13}$ id=1580 2007, 1.

Unknown,, "Standard Test Method for Acid Number of Petroleum Products by Potentiometric Titration", *ASTM International, Designation*: D664-04 Mar. 2004, 1-7.

Verkade, J. G. et al., "Nanoporous Solid Catalysts for Conversion of Soybean Oil to Biodiesel", *Center for Catalysis, Iowa State University* http://www.iprt.iastate.edu/ccat/nano.html Feb. 22, 2006, 1-4.

Vieitez, Ignacio et al., "Continuous Production of Soybean Biodiesel in Supercritical Ethanol-Water Mixtures", *American Chemical Society, Energy & Fuels* Jun. 17, 2008, pp. 1-5.

Xie, W. et al., "Synthesis of Biodiesel from Soybean Oil Using Heterogeneous KF/ZnO Catalyst", *Catalyst Letters* Feb. 2006, 107: 53-59.

Yokoyama, Shin-Ya et al., "Liquid Fuel Production from Ethanol Fermentation Stillage", *Chemistry Letters* 1986, pp. 649-652.

Zhang, P., "A New Process for Biodiesel Production Based on Waste Cooking Oils and Heterogeneous Catalysts", *USDA-SBIR Agreement* #2005-33610-15497 2005, 1-2.

METHODS AND COMPOSITIONS FOR REFINING LIPID FEED STOCKS

This application claims the benefit of U.S. Provisional Application No. 60/976,174, filed Sep. 28, 2007, the contents of which are herein incorporated by reference.

FIELD OF THE INVENTION

The present invention relates to the production of fatty acid alkyl esters from lipid feed stocks. More specifically, the present invention relates to systems and methods of using fatty acid alkyl ester solutions to refine feed stocks before converting the feed stocks into fatty acid alkyl esters.

BACKGROUND OF THE INVENTION

The term "biodiesel" refers to a diesel-equivalent, processed fuel derived from biological sources, such as vegetable oils and/or animal fats. Biodiesel is a processed fuel that can be readily used in vehicles with diesel engines. Biodiesel can be used in pure form or may be blended with petroleum diesel at any concentration in most modern diesel engines.

Biodiesel typically includes the alkyl esters of fatty acids (or fatty acid alkyl esters). The alkyl group is commonly methyl, ethyl, propyl, or isopropyl, although it can also include higher numbers of carbon atoms. Fatty acid alkyl esters can be produced from fats or oils via catalyzed or uncatalyzed reactions. Many existing techniques for producing biodiesel rely on the use of relatively expensive high quality feed stocks such as soybean oil, which are usually greater than 99% triglycerides and 1% or less free fatty acids.

Since feed stock cost is a major component of the overall cost of producing biodiesel fuels, it can be significantly more economical to produce biodiesel from lower cost feed stocks. Unfortunately, many low cost feed stocks are not conducive to the biodiesel production processes. For example, some low cost feed stocks include contaminant materials that can interfere with the production process such as by plugging fixed bed flow reactors. Some low cost feed stocks are not readily solubilized and therefore may not be conducive to liquid phase processing through a fixed bed flow reactor.

SUMMARY OF THE INVENTION

The present invention relates to systems and methods of using fatty acid alkyl ester solutions to refine feed stocks before converting the feed stocks into fatty acid alkyl esters. The present invention also relates to methods of extracting lipid feedstocks from low value products.

In an embodiment, the invention includes a method for producing fatty acid alkyl esters. The method can include mixing a crude lipid feed stock with a refining solution to form a crude product mixture, the refining solution comprising greater than about 10 wt. % fatty acid alkyl esters. The method can include extracting the liquid phase from the crude product mixture to obtain a purified lipid feed stock. The method can also include reacting the purified lipid feed stock with an alcohol to form a product mixture comprising fatty acid alkyl esters.

In an embodiment, the invention includes a method for producing fatty acid alkyl esters. The method can include mixing a crude lipid feed stock with a fatty acid alkyl ester product mixture to form a crude product mixture. The method can also include extracting the liquid phase from the crude product mixture to obtain a purified lipid feed stock. The method can also include mixing the purified lipid feed stock with an alcohol to form a reaction mixture and contacting the reaction mixture with a metal oxide catalyst to form the crude product mixture.

In an embodiment, the invention includes a method of refining a crude lipid feed stock. The method can include mixing a crude lipid feed stock with a refining solution to form a crude product mixture, the refining solution comprising greater than about 10 wt. % fatty acid alkyl esters. The method can also include extracting the liquid phase from the crude product mixture to obtain a purified lipid feed stock.

In an embodiment, the invention includes a method of refining a crude lipid feed stock. The method can include mixing a crude lipid feed stock with a biodiesel solution to form a crude product mixture. The method can also include extracting the liquid phase from the crude product mixture to obtain a purified lipid feed stock.

In an embodiment, the invention includes a method of making a fatty acid alkyl ester composition. The method can include extracting lipids from a corn-based ethanol production byproduct, adding an alcohol solution to the lipids to form a reaction mixture, and contacting the reaction mixture with a metal oxide catalyst.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

Figure 1:
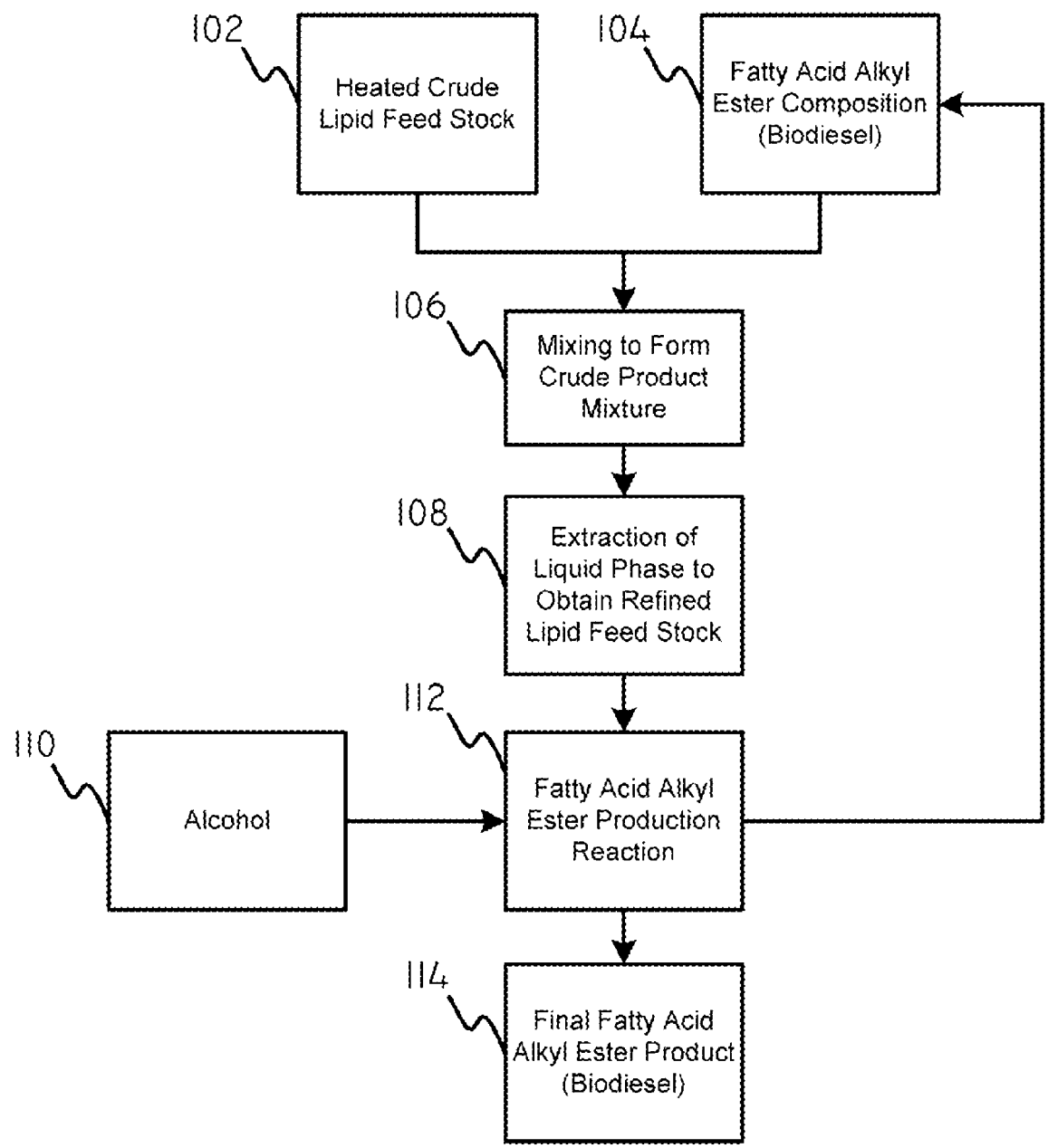
FIG. 1 is a schematic view of a method of producing fatty acid alkyl esters in accordance with an embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As described above, it can be economically desirable to produce fatty acid alkyl esters from low cost feed stocks. However, low cost feed stocks are frequently difficult to process because of impurities, residues, contaminants, and other components in the crude feed stocks that may interfere with the production process.

However, as shown in the examples below, Applicants have discovered that fatty acid alkyl ester compositions can serve as desirable refining agents for use in preprocessing low cost feed stocks. In other words, the end product of the fatty acid alkyl ester production process itself can be used as an effective pretreatment to separate desirable feed stock components from undesirable insoluble feed stock components.

The use of a fatty acid alkyl ester composition as a refining agent offers several advantages. One advantage is that it eliminates the need for a potentially costly recovery step. For example, some solvents that could be used, such as hexane, would have to be recovered from the reaction product mixture in a recovery step. Such a recovery step can make the process more expensive and the volatility of some solvents can make it more dangerous (explosive). In contrast, the flammability (flash point) is higher and volatility is lower for biodiesel fatty acid alkyl esters.

Another advantage is that fatty acid alkyl esters are not damaged or converted into undesirable byproducts under the reaction conditions used to produce biodiesel.

Yet another advantage is that production plants using fatty acid alkyl ester compositions as a refining agent do not need to keep a supply of yet another component on hand. Since a fatty acid alkyl ester composition is itself an end product of the production process, some of the reaction products can simply be routed back for use with the initial feed stock refining operation. In contrast, the use of other types of solvents may require a separate supply input to the production plant resulting in additional transactional and storage burden.

Another advantage of the extraction of feedstocks with fatty acid alkyl esters is that often times the crude feedstocks are a solid at room temperature, but extraction converts them to a liquid form at room temperature which is then amenable to various biodiesel production process. The fact that the feedstock is converted to a liquid from by extraction also means that it is not necessary to heat the feedstock (or use less heat), which saves on overall energy costs.

Applicants have also discovered that lipid feedstocks can be extracted from some low value waste products through techniques such as centrifugation. These extracted lipid feedstocks can then be converted into fatty acid alkyl ester compositions (biodiesel). For example, Applicants have discovered that a lipid feedstock can be recovered from corn distillers syrup (CDS), which is byproduct of corn-based ethanol production processes. Treatment of the CDS, such as through centrifugation, yields a lipid feedstock that is relatively high in free fatty acid content. The CDS lipid feedstock can then be used to produce a fatty acid alkyl ester composition using metal oxide catalysts. Exemplary metal oxide catalysts and methods of producing fatty acid alkyl ester compositions (biodiesel) can be found in U.S. Publ. Pat. Appl. No. 2008/0051592, entitled "METHODS AND APPARATUS FOR PRODUCING ALKYL ESTERS FROM LIPID FEED STOCKS AND SYSTEMS INCLUDING SAME", the content of which is herein incorporated by reference.

Referring now to FIG. 1, a flowchart of an exemplary process of producing fatty acid alkyl esters is shown. In a first operation 102, a crude lipid feed stock is heated. In a second operation 104, a fatty acid alkyl ester composition is obtained. In some embodiments, the fatty acid alkyl ester composition is obtained as a reaction product of the process itself. The fatty acid alkyl ester composition can have a percentage by weight of fatty acid alkyl esters equal to or greater than about 10 percent.

The heated crude lipid feed stock and the fatty acid alkyl ester composition are then mixed together to form a crude product mixture in a third operation 106. The fatty acid alkyl ester composition can act to solubilize components in the crude feed lipid feed stock (glycerides and free fatty acids), as shown below in Example 4.

In a fourth operation 108, liquid phase components are separated from insoluble components forming a refined lipid feed stock. It will be appreciated that this separation operation can be conducted in many different ways. For example, in some embodiments, centrifugation is used to perform the separation. In some embodiments, filtration is used to perform the separation. In still other embodiments, a distillation process is used to perform the separation. In some embodiments, a combination of techniques is used, for example centrifugation can be performed followed by filtration. The separation operation can be performed continuously or in batches.

In some embodiments, only a single separation operation is performed. In other embodiments, multiple separation operations can be performed. In addition, in some embodiments, additional amounts of a fatty acid alkyl ester composition can be used in order to solubilize a greater percentage of the original crude lipid feed stock. For example, in some embodiments after the liquid phase is removed in a first separation operation, the remaining components can be combined with an additional amount of a fatty acid alkyl ester composition and then a second separation operation can be performed. In some embodiments, these successive operations can be repeated three or more times.

After separation, fatty acid alkyl esters can be produced from the refined lipid feed stock in a fifth operation 112. An alcohol 110, such as a C1-C6 alcohol, is utilized as an input in the fatty acid alkyl ester production reaction. The reaction can be catalyzed. By way of example, the reaction can be catalyzed with a metal oxide catalyst. Exemplary metal oxide catalysts can include alumina, titania, zirconia, and hafnia. Exemplary catalysts, reaction conditions, and reactors are further described in U.S. Publ. Pat. Appl. No. 2008/0051592, entitled "Methods and Apparatus for Producing Alkyl Esters from Lipid Feed Stocks and Systems Including the Same", the content of which is herein incorporated by reference. After the reaction takes place, some of the fatty acid alkyl ester product can be diverted for reuse in the process of refining the crude feed stock. The remainder of the fatty acid alkyl ester product can form the final fatty acid alkyl ester product.

In some embodiments, various other processing steps may be performed. By way of example, the fatty acid alkyl ester product composition may be further processed in order to render it suitable for use as biodiesel fuel. For example, in some embodiments, free fatty acids remaining in the fatty acid alkyl ester product composition are removed. Exemplary techniques for removing free fatty acids are described in U.S. Publ. Pat. Appl. No. 2008/0197052, entitled "Devices and Methods for Selective Removal of Contaminants from a Composition", the content of which is herein incorporated by reference. In some embodiments, additional separation steps are performed after the fatty acid alkyl ester production reaction. By way of example, a centrifugation step can be performed in order to remove byproducts such as glycerol from the fatty acid alkyl ester product composition. In some embodiments, volatile byproducts from the fatty acid alkyl ester production reaction are captured and sold or burned off.

Figure 2:
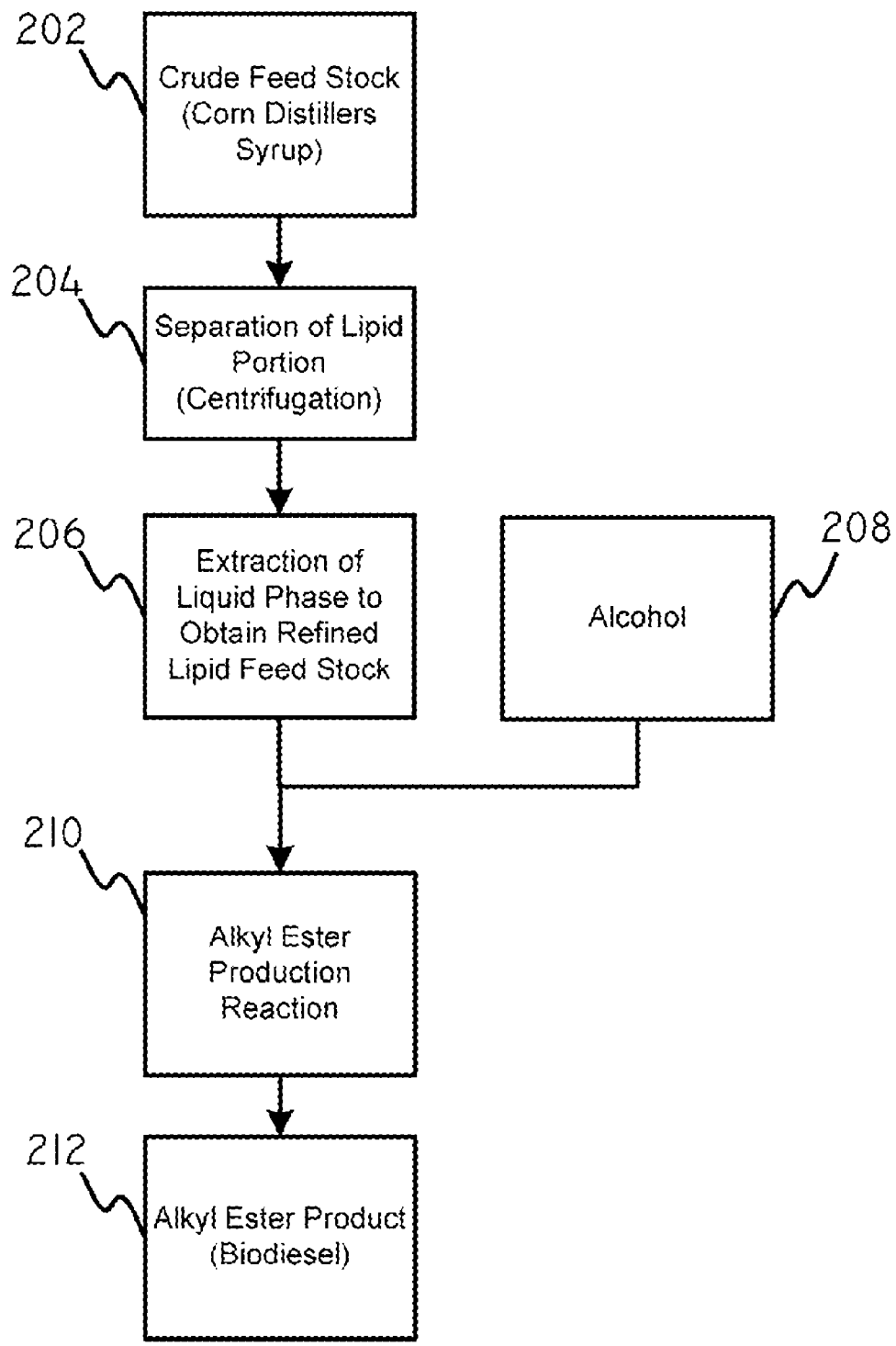
FIG. 2 is a schematic view of a method of producing fatty acid alkyl esters in accordance with an embodiment of the invention.

Referring now to FIG. 2, a flowchart of an exemplary process of producing fatty acid alkyl esters in accordance with another embodiment is shown. In a first operation 202, a crude feed stock is obtained. An exemplary crude feed stock is corn distillers syrup, though other possible feedstocks are described below. In a second operation 204, the lipid portion of the crude feedstock is separated from the other components. An exemplary technique that can be used for separation is centrifugation, though it will be appreciated that other separation techniques can also be used.

In a third operation 206, the liquid phase (lipid portion of the crude feedstock) is extracted to obtain a refined lipid feedstock. In some embodiments, extraction may include simply decanting off the liquid phase. In some embodiments, extraction can include the performance of other steps such as solvent based extraction, filtration, distillation and the like. In a fourth operation 210, a fatty acid alkyl ester product 212 can be produced from the refined lipid feedstock and an alcohol

208, such as a C1-C6 alcohol. The reaction can be catalyzed. By way of example, the reaction can be catalyzed with a metal oxide catalyst. Exemplary metal oxide catalysts can include alumina, titania, zirconia, and hafnia. Exemplary catalysts, reaction conditions, and reactors are further described in U.S. Publ. Pat. Appl. No. 2008/0051592, entitled "Methods and Apparatus for Producing Alkyl Esters from Lipid Feed Stocks and Systems Including the Same", the content of which is herein incorporated by reference.

Lipid Feed Stocks

Lipid feed stocks used with embodiments of the invention can specifically include low value/low cost feed stocks. By way of example, low value/low cost feed stocks can include soap stock, acidulated soap stock, waste oils (such as brown and yellow grease), and animal tallow (such as swine, beef, and poultry tallow) and wet distillers grain and syrup produced in the commercial production of ethanol.

Some low value feed stocks, such as various types of animals fats and waste oils, generally have a relatively high concentration of free fatty acids. One method of assessing the concentration of free fatty acids is to determine the acid number (or acid value) of the feed stock. The acid number is the mass of potassium hydroxide (KOH) in milligrams that is required to neutralize one gram of the chemical substance being assessed. Acid number can be assessed according to ASTM D664. The precise acid number as measured can vary because of the heterogeneity of the lipid feed stock. However, as an example, a high value feed stock such as virgin soybean oil can have an acid number of about 0.35 whereas a lower value feed stock such as swine tallow can have an acid number of about 5. Yellow grease, a low value feed stock, can have an acid number of about 15. The oil extracted from corn distillers syrup can have an acid number of about 27.5 (in contrast to virgin corn oil which has an acid number of approximately 0.06). Acidulated soap stock, also a low value feed stock; can have an acid number of about 88 or higher. Acid numbers for various lipid feed stocks are shown below in Table 1.

TABLE 1

| Feedstock | Source | Acid Number | Initial State (room temp) |
|---|---|---|---|
| Acidulated Soapstock | Plant | 88.20 | Liquid |
| Yellow Grease | Mixed | 15.26 | Mixed |
| Refined Lard | Animal | 7.88 | Solid |
| Swine Tallow | Animal | 5.11 | Solid |
| Walnut Oil | Plant | 4.47 | Liquid |
| Sesame Oil | Plant | 3.00 | Liquid |
| Refined Algae Oil | Plant | 0.71 | Mixed |
| Olive Oil | Plant | 0.46 | Liquid |
| Soybean Oil | Plant | 0.35 | Liquid |
| Palm Oil | Plant | 0.25 | Solid |
| Almond Oil | Plant | 0.19 | Liquid |
| Grape Seed Oil | Plant | 0.12 | Liquid |
| Rice Oil | Plant | 0.09 | Liquid |
| Sunflower Oil | Plant | 0.08 | Liquid |
| Corn Oil | Plant | 0.06 | Liquid |
| Canola Oil | Plant | 0.05 | Liquid |
| Peanut Oil | Plant | 0.05 | Liquid |
| Safflower Oil | Plant | 0.05 | Liquid |
| Coconut Oil | Plant | 0.04 | Solid |

Systems and methods of the invention can advantageously use low value feed stocks in order to produce biodiesel fuel while achieving high percent conversion rates. In some embodiments, the lipid feed stock used has an acid number of about 3 (mg KOH/g oil) or greater. In some embodiments, the lipid feed stock used has an acid number of about 5 (mg KOH/g oil) or greater. In some embodiments, the lipid feed stock used has an acid number of about 10 (mg KOH/g oil) or greater. In some embodiments, the lipid feed stock used has an acid number of about 50 (mg KOH/g oil) or greater.

Beyond low value feed stocks, it will be appreciated that many different lipid feed stocks can be used in embodiments of the invention. In some embodiments, lipid feed stocks used in embodiments of the invention can include biological lipid feed stocks. Biological lipid feed stocks can include lipids (fats or oils) produced by any type of microorganism, plant or animal. In an embodiment, the biological lipid feed stocks used include triglycerides. Many different biological lipid feed stocks derived from plants can be used. By way of example, plant-based lipid feed stocks can include rapeseed oil, soybean oil (including degummed soybean oil), canola oil, cottonseed oil, grape seed oil, mustard seed oil, corn oil, linseed oil, safflower oil, sunflower oil, poppy-seed oil, pecan oil, walnut oil, oat oil, peanut oil, rice bran oil, camellia oil, castor oil, and olive oil, palm oil, coconut oil, rice oil, algae oil, seaweed oil, Chinese Tallow tree oil. Other plant-based biological lipid feed stocks can be obtained from argan, avocado, babassu palm, balanites, borneo tallow nut, brazil nut, calendula, camelina, caryocar, cashew nut, chinese vegetable tallow, cocoa, coffee, cohune palm, coriander, cucurbitaceae, euphorbia, hemp, illipe, jatropha, jojoba, kenaf, kusum, macadamia nuts, mango seed, noog abyssinia, nutmeg, opium poppy, perilla, pili nut, pumpkin seed, rice bran, sacha inche, seje, sesame, shea nut, teased, allanblackia, almond, chaulmoogra, cuphea, jatropa curgas, karanja seed, neem, papaya, tonka bean, tung, and ucuuba, cajuput, clausena anisata, davana, galbanum natural oleoresin, german chamomile, hexastylis, high-geraniol monarda, juniapa-hinojo sabalero, lupine, melissa officinalis, milfoil, ninde, patchouli, tarragon, and wormwood.

Many different lipid feed stocks derived from animals can also be used. By way of example, animal-based biological lipid feed stocks can include choice white grease, lard (pork fat), beef tallow (beef fat), fish oil, and poultry fat.

Many different lipid feed stocks derived from microorganisms (such as Eukaryotes, Eubacteria and Archaea) can also be used. By way of example, microbe-based lipid feed stocks can include the L-glycerol lipids of Archaea and algae and diatom oils.

In some embodiments, lipid feed stocks derived from both plant and animal sources can be used such as yellow grease, white grease, and brown grease. By way of example, yellow, white or brown grease can include frying oils from deep fryers and can thus include fats of both plant and animal origin. Lipid feed stocks can specifically include used cooking oil. Brown grease (also known as trap grease) can include fats extracted from sewage systems and can thus include fats of both plant and animal origin. In some embodiments, lipid feed stocks used in embodiments of the invention can include non-biological lipid feed stocks. Lipid feed stocks of the invention can include black oil which comes from oilseed crushing plants.

In some embodiments herein fatty acid alkyl esters (biodiesel) can be used as a solvent instead of traditional solvent extraction methods for the liberation of vegetable oils from crops such as soybean, sunflowers and canola. In such embodiments, the crop is first crushed and then extracted with fatty acid alkyl esters and then the resulting mash is put through a continuous centrifuge to spin off the liquid. The liquid can then be further refined by centrifugation to produce a feedstock that can be used in a process for the production of alkyl esters (e.g. biodiesel).

Alcohols

Alcohols used in some embodiments of the invention can include many different types of alcohols. By way of example, alcohols used in some embodiments of the invention can include alcohols having from one to six carbon atoms. For example, in some embodiments, methanol is used. Methanol can be advantageous as the resulting fatty acid alkyl esters (fatty acid methyl esters) have a lower viscosity than higher fatty acid alkyl esters. However, in some embodiments ethanol is used. Ethanol has low toxicity and is readily produced from plant matter by fermentation processes.

In some embodiments, a single alcohol is used. In other embodiments, a mixture of different alcohols is used. By way of example, a mixture of methanol and a higher molecular weight alcohol can be used. Such a mixture can offer the advantage of being more miscible with the biological lipid feed stock than methanol alone.

The present invention may be better understood with reference to the following examples. These examples are intended to be representative of specific embodiments of the invention, and are not intended as limiting the scope of the invention.

EXAMPLES

Example 1

Production of Fatty Acid Alkyl Ester Composition from Unrefined Lipid Feed Stock A.) Formation of Base Modified Titania Particles 700 mL of 1.0 M sodium hydroxide was added to a 2 liter plastic Erlenmeyer flask. Next, 110 g of 80 µm/60 Å titania, purchased from ZirChrom Separations, Inc., Anoka, Minn. 55303, was added to the flask. The particle suspension was sonicated for 10 minutes under vacuum and then swirled for 2 hours at ambient temperature. The particles were then allowed to settle and the base solution was decanted. Then 1.4 liters of HPLC-grade water was added to the flask and stirred followed by settling and decanting. Then 200 mL of HPLC-grade water was added back to the flask and the particles were collected on a MILLIPORE nylon filter with 0.45 micron average pores. The collected particles were then washed with 2 aliquots of 200 mL HPLC-grade water followed by 3 aliquots of 200 mL of HPLC-grade methanol. Air was then allowed to flow through the particles until they were dry and free-flowing.

B.) Reactor Packing

Particles as formed in step A were dry-packed into two of 15 cm×10.0 mm i.d. stainless steel reactor tubes forming a MCGYAN™ Reactor. Each such MCGYAN™ Reactor contained 16.3 g of washed titania (Batch No. 60-156).

C.) Treatment of Acidulated Soapstock

Raw acidulated soapstock was obtained from ADM, Enderlin, N. Dak. It was heated to 90° C. to form an acidulated soapstock liquid. The heated acidulated soapstock liquid was filtered rapidly through a 5 micron membrane.

D.) Continuous Production of Biodiesel from Methanol and Acidulated Soapstock Liquid Feed Stock Using Based Washed Titania Catalyst A heat exchange system was used to both heat the reactants (the filtered acidulated soapstock from the previous step and methanol) and cool the reaction products. A coil preheater was used to raise the temperature of reactants (acidulated soapstock liquid and methanol) before entering the titania packed stainless steel reactor (MCGYAN™ Reactor). The acidulated soapstock liquid and methanol preheater included tubing wound around a grooved heater core with a resistive heater disposed in the middle of the core. A thermocouple was used to monitor the preheater core temperature. A reactor heater was used to regulate the temperature of the reactor. The reactor heater was a tube furnace heater.

Both feed stock supply vessels, containing acidulated soapstock liquid and the methanol respectively, were sparged with nitrogen gas in order to remove any dissolved oxygen from the feed stocks. The acidulated soapstock liquid and methanol were separately pumped, at the flow rates indicated below. The flow streams were then joined at elevated temperature and pressure via a "T". The mixed reactant flow streams then passed through a heat exchanger and preheater before entering the titania catalyst filled stainless steel tube fixed bed reactor (MCGYAN™ Reactor). A back pressure regulator was used to maintain elevated pressure within the MCGYAN™ Reactor. The reaction temperatures are summarized in Table 2. The methanol flow rate was set at 9.088 ml/min and the biodiesel extracted acidulated soapstock liquid flow rate was set at 6.151 ml/min.

TABLE 2

| | Temperature (Degrees Celsius) | | | | | | | |
|---|---|---|---|---|---|---|---|---|
| Experiment | Setting Point | Preheater | Reactor Inlet | Between Reactors | Reactor Outlet | Before Heat Exchanger | After Heat Exchanger | At "T" |
| 1 | 360 | 356 | 343 | 325 | 329 | 202 | 77 | 105 |
| 2 | 360 | 363 | 348 | 332 | 336 | 208 | 86 | 110 |
| 3 | 360 | 363 | 348 | 338 | 339 | 209 | 94 | 115 |
| 4 | 360 | 356 | 347 | 341 | 341 | 207 | 96 | 116 |
| 5 | 360 | 366 | 352 | 343 | 343 | 206 | 98 | 117 |
| 6 | 360 | 356 | 342 | 331 | 337 | 202 | 96 | 113 |
| 7 | 370 | 367 | 346 | 330 | 334 | 202 | 94 | 114 |
| 8 | 370 | 362 | 351 | 331 | 336 | 207 | 94 | 116 |

Pressures and sampling times for the experiments are shown in Table 3. Conversion to fatty acid methyl esters was assessed using NMR. The conversion data are shown in Table 3.

TABLE 3

| | Pressure (PSI) | | Sampling Time | Conversion |
|---|---|---|---|---|
| Experiment | Front | Back | (min) | % (NMR) |
| 1 | 3400 | 2700 | 39 | 90.1 |
| 2 | 3500 | 2700 | 47 | 85.8 |
| 3 | 3650 | 2700 | 61 | 89.7 |

TABLE 3-continued

| Experiment | Pressure (PSI) Front | Pressure (PSI) Back | Sampling Time (min) | Conversion % (NMR) |
|---|---|---|---|---|
| 4 | 3500 | 2700 | 71 | 88.9 |
| 5 | 3450 | 2700 | 81 | 93.5 |
| 6 | 3500 | 2700 | 81 | 84.7 |
| 7 | 3600 | 2700 | 128 | 90.5 |
| 8 | 3800 | 2700 | 172 | 86.6 |

For each experiment conducted in Example 1, it was observed that the pressure measured before the reactor gradually increased from approximately 2700 psi to 4100 psi over the sampling time. This increase in pressure is indicative of reactor plugging. As such, this example shows that unrefined acidulated soapstock, a low value lipid feed stock, can be used to make fatty acid alkyl ester compositions, however, the unrefined acidulated soapstock plugs up the reactor, even after performing a filtration step.

Example 2

Production of Fatty Acid Alkyl Ester Composition from Lipid Feed stock Refined with Biodiesel Composition A.) Preparation of Unmodified Titania Particles 110 g of 80 μm/60 Å titania was obtained from ZirChrom Separations, Inc., Anoka, Minn. 55303. The particles were suspended into 500 mL deionized water. The particle suspension was sonicated for 10 minutes under vacuum and then swirled for 2 hours at ambient temperature. The particles were then allowed to settle and the solution was decanted to remove the fine particles, and then 0.5 liters of HPLC-grade water was added to the flask followed by settling and decanting. Then, 200 mL of HPLC-grade water was added back to the flask and the particles were collected on a MILLIPORE nylon filter with 0.45 micron average pores. The collected particles were then washed with 2 aliquots of 200 mL HPLC-grade water followed by 3 aliquots of 200 mL of HPLC-grade methanol. Air was then allowed to flow through the particles until they were dry and free-flowing.

B.) Reactor Packing

Two reactors were prepared as described in Example 1, using the unmodified titania particle prepared in the previous step.

C.) Refining of Acidulated Soapstock

Raw acidulated soapstock was obtained from CHS Inc. (2020 South Riverfront Drive, Mankato, Minn. 56002). The acidulated soapstock was heated to 50° C. to make a soapstock liquid. A 1398.77 g sample of the acidulated soapstock liquid was mixed into 1397.92 g of a fatty acid alkyl ester composition (greater than about 88 wt. % fatty acid alkyl esters, acid number 5.7) to form an acidulated soapstock-biodiesel extract solution. The acidulated soapstock-biodiesel extract solution was warmed at 50° C. for 10 minutes. The acidulated soapstock-biodiesel extract solution was then allowed to stand at ambient temperature overnight. Next the acidulated soapstock-biodiesel extract solution was centrifuged at 10,000 rpm (12,857 G) for 6 minutes. After centrifuging, the supernatant was filtered through a 5 micron membrane.

D.) Continuous Production of Biodiesel from Acidulated Soapstock-Biodiesel Extract and Methanol Using Unmodified Titania Catalyst A heat exchange system was used to both heat the reactants (refined and filtered acidulated soapstock-biodiesel extract liquid from previous step and methanol) and cool the reaction products. A coil preheater was used to raise the temperature of reactants before entering the titania packed stainless steel MCGYAN™ reactor. The preheater included tubing wound around a grooved heater core with a resistive heater disposed in the middle of the core. A thermocouple was used to monitor the preheater core temperature. A reactor heater was used to regulate the temperature of the MCGYAN™ reactor. The MCGYAN™ reactor heater was a tube furnace heater.

Both the soapstock-biodiesel extract liquid vessel and the methanol vessel were sparged with nitrogen gas. The acidulated soapstock-biodiesel liquid and methanol were separately pumped, at the flow rates indicated below. The flow streams were then joined and passed through a heat exchanger, preheater and then into the titania stainless steel MCGYAN™ reactor. Pressure regulators were used to maintain pressure within the MCGYAN™ reactor as indicated. The reaction conditions are summarized in Tables 4 and 5. The methanol flow rate was set at 9.088 ml/min and the acidulated soapstock-biodiesel liquid flow rate was 6.151 ml/min. The conversion to biodiesel is also shown in Table 4 as measured by NMR. A sample of the resulting biodiesel produced was submitted to a testing laboratory (FuelOnly, Inc., Vancouver, Wash.) for analysis. The analysis showed that the biodiesel produced met ASTM specifications (including ASTM tests D1160, D6584, D4530, D664, D2709, D5453, D976, D445, D93, D2500, D874, D613, and D4951) for biodiesel fuel.

TABLE 4

| | Temperature (Degrees Celsius) | | | | | | | |
|---|---|---|---|---|---|---|---|---|
| Experiment | Setting Point | Preheater | Reactor Inlet | Between Reactors | Reactor Outlet | Before Heat Exchanger | After Heat Exchanger | At "T" |
| 9 | 290 | 290 | 290 | 282 | 285 | 244 | 95 | 205 |
| 10 | 290 | 290 | 290 | 282 | 285 | 244 | 95 | 205 |
| 11 | 290 | 290 | 290 | 282 | 285 | 244 | 95 | 205 |
| 12 | 290 | 290 | 290 | 282 | 285 | 244 | 95 | 205 |

TABLE 5

| Experiment | Pressure (PSI) Front | Pressure (PSI) Back | Sampling Time (min) | Conversion % (NMR) |
|---|---|---|---|---|
| 9 | 2650 | 2500 | 68 | 83 |
| 10 | 2650 | 2500 | 93 | 83 |
| 11 | 2650 | 2500 | 118 | 83 |
| 12 | 2650 | 2500 | 134 | 83 |

For each experiment conducted in Example 2, it was observed that the pressure measured before the remained largely constant over the sampling time. This constant pressure is indicative of the reactor remaining free from obstruction. This observation stands in contrast to the increase in pressure observed with the reactor in Example 1. As such, this example shows that refining of a crude lipid feed stock with an fatty acid alkyl ester composition can improve the production process at least because the reactor is not as susceptible to plugging when using a refined lipid feed stock.

Example 3

Production of Fatty Acid Alkyl Ester Composition from Lipid Feed Stock Refined with Biodiesel Composition Containing Alcohol A.) Preparation of Unmodified Modified Titania Particles Titania particles were prepared as described in Example 2 above.

B.) Reactor Packing

Two reactors were prepared as described in Example 2 above.

C.) Refining of Acidulated Soapstock

Raw acidulated soapstock was obtained from CHS Inc., Mankato, Minn. The acidulated soapstock was heated to 50° C. to make a liquid acidulated soapstock. A 1456.94 g sample of the liquid acidulated soapstock was added into 1455.83 g of as-made biodiesel containing approximately 8% methanol. The as made biodiesel was produced at SarTec's biodiesel pilot plant employing the MCGYAN™ process. The biodiesel/acidulated soap stock extract liquid, was warmed at 50° C. for 10 minutes. The solution was then allowed to stand, at ambient temperature, for two days. After centrifuging the acidulated soapstock-biodiesel liquid at 10,000 rpm (12,857 G) for 6 minutes the liquid was filtered through a 5 um membrane filter. The total mass recovery of the filtrate was about 93%.

D.) Continuous Production of Biodiesel from Methanol and Acidulated Soapstock-Biodiesel Extract Using Unmodified Titania Catalyst Biodiesel was then produced from the acidulated soapstock-biodiesel extract as described in Example 2 above. The reaction conditions are summarized in Tables 6 and 7. Methanol flow rate was set at 9.088 ml/min and the soapstock-biodiesel extract feed stock flow rate was 6.151 ml/min. The conversion to biodiesel is also shown in Table 7 as measured by NMR.

TABLE 6

| | Temperature (Degrees Celsius) | | | | | | | |
|---|---|---|---|---|---|---|---|---|
| Experiment | Setting Point | Preheater | Reactor Inlet | Between Reactors | Reactor Outlet | Before Heat Exchanger | After Heat Exchanger | At "T" |
| 13 | 290 | 290 | 290 | 283 | 286 | 245 | 98 | 206 |
| 14 | 290 | 290 | 290 | 282 | 285 | 244 | 101 | 208 |
| 15 | 290 | 290 | 290 | 283 | 285 | 244 | 100 | 207 |
| 16 | 290 | 290 | 290 | 283 | 285 | 244 | 100 | 207 |
| 17 | 290 | 290 | 290 | 283 | 285 | 244 | 100 | 207 |

TABLE 7

| Experiment | Pressure (PSI) Front | Pressure (PSI) Back | Sampling Time (min) | Conversion % (NMR) |
|---|---|---|---|---|
| 13 | 2650 | 2500 | 230 | 80.6 |
| 14 | 2650 | 2500 | 321 | 84.4 |
| 15 | 2650 | 2500 | 346 | 83 |
| 16 | 2650 | 2500 | 410 | 83.7 |
| 17 | 2650 | 2500 | 434 | 84 |

For each experiment conducted in Example 3, it was observed that the pressure measured before the reactor remained largely constant over the sampling time. This constant pressure is indicative of the reactor remaining free from obstruction. This observation stands in contrast to the increase in pressure observed with the reactor in Example 1. As such, this example shows that refining of a crude lipid feed stock with an fatty acid alkyl ester composition can improve the production process at least because the reactor is not as susceptible to plugging when using a refined lipid feed stock.

Example 4

Repeated Extraction of Acidulated Soapstock With Fatty Acid Alkyl Ester Composition A sample of acidulated soapstock (1882.41 g) was added to a flask along with 1880.23 g of a fatty acid alkyl ester composition (biodiesel, containing greater than about 88 wt. % fatty acid alkyl esters) to create a 50/50 mixture. The mixture was heated to a temperature of 50° C. degrees Celsius for approximately 15 minutes. The mixture was then centrifuged and the supernatant was decanted off. The insoluble materials were collected after centrifugation and weighed. It was found that of the total weight of components in the mixture, the liquid phase accounted for approximately 90 wt. % and the insoluble sludge accounted for approximately 10 wt. %.

The insoluble sludge (20 g) was then added to a flask along with 80 g of a fatty acid alkyl ester composition (biodiesel) to create a 80/20 (biodiesel/insolubles) mixture. The mixture was shaken for 2 minutes. The mixture was then centrifuged and the supernatant was decanted off. It was found that of the total weight of components in the mixture, the liquid phase accounted for approximately 91 wt. % and the insoluble sludge accounted for approximately 9 wt. %.

The resulting insoluble sludge (3 g) was then added to a flask along with 7 g of a fatty acid alkyl ester composition (biodiesel) to create a 70/30 (biodiesel/insolubles) mixture. The mixture was shaken for 2 minutes. The mixture was then centrifuged and the supernatant was decanted off. It was found that of the total weight of components in the mixture, the liquid phase accounted for approximately 76 wt. % and the insoluble sludge accounted for approximately 24 wt. %.

After extraction with the fatty acid alkyl ester composition for another two times and a final extraction performed with hexane, about 0.33 wt. % of the original acidulated soapstock remained insoluble.

Example 5

Extraction of Oil from Corn Distillers Syrup

Corn distillers syrup is a byproduct of corn-based ethanol production processes. A sample of corn distillers syrup was obtained from a commercial ethanol production plant. Fatty acid alkyl ester compositions were added to samples of the corn distillers syrup in various proportions to a combined amount of 40 grams. Then the resulting mixture was shaken for approximately two minutes. The specific amounts are provided in Table 8 below.

TABLE 8

| Trial Number (# of samples) | Amount of Alkyl Ester Composition (grams) | Amount of Corn Distillers Syrup (grams) |
| --- | --- | --- |
| 1 (n = 6) | 2 | 38 |
| 2 (n = 3) | 4 | 36 |
| 3 (n = 3) | 8 | 32 |

After shaking, the mixtures were allowed to stand for approximately 30 minutes at room temperature. Three of the samples from trial 1 were allowed to stand for an extra period of time at room temperature (identified in Table 9 below as Trial Number 1b). Next, all of the samples were centrifuged for six minutes at approximately 12857 g. After centrifugation, the liquid phase was decanted off and weighed. The results are shown below in Table 9.

TABLE 9

| Trial Number | Final Avg. Weight (grams) | Avg. Weight of Oil Extracted (grams) | Avg. Oil Extracted as Percentage of CDS |
| --- | --- | --- | --- |
| 1a | 3.09 | 1.09 | 2.86% |
| 1b | 3.63 | 1.63 | 4.28% |
| 2 | 5.54 | 1.54 | 4.27% |
| 3 | 9.14 | 1.14 | 3.57% |

This example shows that fatty acid alkyl ester compositions can be used to extract significant amounts of feedstock oils from low value byproducts such as corn distillers syrup (CDS).

Example 6

Extraction of Oil from Corn Distillers Syrup via Centrifugation

A sample of corn distillers syrup (CDS) was obtained from a commercial ethanol production plant. Six samples of the corn distillers syrup were weight and centrifuged at approximately 12857 g for approximately six minutes. The liquid phase (lipids) was then decanted off after centrifugation and weighed. The results are shown in Table 10 below.

TABLE 10

| CDS (g) | Lipids (g) | % (w/w) Lipids in CDS |
| --- | --- | --- |
| 41.46 | 1.46 | 3.5% |
| 41.52 | 1.44 | 3.5% |
| 41.38 | 1.52 | 3.7% |
| 41.48 | 1.48 | 3.6% |
| 41.18 | 1.51 | 3.7% |
| 41.43 | 1.54 | 3.7% |

The acid number of the liquid phase (lipids) was then assessed according to ASTM D664 and determined to be approximately 27.5. This example shows that a lipid feedstock with a relatively high acid number can be extracted from ethanol production byproducts such as corn distillers syrup.

The invention has been described with reference to various specific and preferred embodiments and techniques. However, it should be understood that many variations and modifications may be made while remaining within the spirit and scope of the invention. While reference is made to the production of biodiesel fuel, it will be appreciated the production of esters has significant commercial application outside the context of fuel production. As such, the invention can also include embodiments directed to the production of esters via esterification and transesterification reactions in other many other contexts.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The claims are:

1. A method of making a fatty acid alkyl ester composition, the method comprising:
    extracting lipids from a corn-based ethanol production byproduct;
    adding an alcohol solution to the lipids to form a reaction mixture; and
    contacting the reaction mixture with a metal oxide catalyst.

2. The method of claim 1, wherein extracting lipids from a corn-based ethanol production byproduct comprises centrifuging the corn-based ethanol production byproduct.

3. The method of claim 1, the corn-based ethanol production byproduct comprising corn distillers syrup.

4. The method of claim 1, wherein contacting the reaction mixture with a metal oxide catalyst is performed under supercritical conditions for the alcohol.

5. The method of claim 1, wherein contacting the reaction mixture with a metal oxide catalyst is performed at a temperature of between about 350 and 400 degrees Celsius.

6. The method of claim 1, wherein contacting the reaction mixture with a metal oxide catalyst is performed at a pressure of between about 1500 and 5000 psi.

7. The method of claim 1, the metal oxide catalyst comprising a material selected from the group consisting of zirconia, titania, hafnia, and alumina.

8. The method of claim 1, the metal oxide catalyst comprising a material selected from the group consisting of zirconia and titania.

9. The method of claim 1, the metal oxide catalyst comprising an unmodified metal oxide.

10. The method of claim 1, the metal oxide catalyst consisting essentially of an unmodified metal oxide selected from the group consisting of alumina, titania, zirconia, and hafnia.

11. The method of claim 1, the metal oxide catalyst consisting essentially of titania.

12. The method of claim 1, the metal oxide catalyst comprising particles with an average particle size of about 0.2 microns to about 2 millimeters.

13. The method of claim 1, the metal oxide catalyst comprising particles with an average particle size of about 1 μm to about 100 μm.

14. The method of claim 1, the alcohol comprising a C1-C6 alcohol.

15. The method of claim 14, the alcohol comprising ethanol.

16. The method of claim 14, the alcohol comprising methanol.

17. The method of claim 1, wherein extracting lipids from a corn-based ethanol production byproduct comprises solvent based extraction.

18. The method of claim 1, wherein contacting the reaction mixture with a metal oxide catalyst is performed with a residence time of less than about 60 seconds.

* * * * *